United States Patent [19]

Jagielinski

[11] Patent Number: 5,105,087
[45] Date of Patent: Apr. 14, 1992

[54] LARGE SOLID STATE SENSOR ASSEMBLY FORMED FROM SMALLER SENSORS

[75] Inventor: Tomasz M. Jagielinski, Carlsbad, Calif.

[73] Assignee: Eastman Kodak Company, Rochester, N.Y.

[21] Appl. No.: 618,810

[22] Filed: Nov. 28, 1990

[51] Int. Cl.$^5$ ............................................. G01N 23/04
[52] U.S. Cl. ........................... 250/370.09; 250/208.1; 250/370.08
[58] Field of Search ............. 250/370.09, 332, 370.08, 250/208.1

[56] References Cited

U.S. PATENT DOCUMENTS

| | | | |
|---|---|---|---|
| 4,467,342 | 8/1984 | Tower | 357/45 |
| 4,755,681 | 7/1988 | Oka et al. | 250/370.09 |
| 4,873,708 | 10/1989 | Cusano et al. | 250/370.09 |

FOREIGN PATENT DOCUMENTS 70482 6/1981 Japan ..................... 370.09/

*Primary Examiner*—Carolyn E. Fields
*Attorney, Agent, or Firm*—William F. Noval

[57] ABSTRACT

A large solid state sensor assembly is formed from a plurality of smaller solid state sensors which are positioned contiguously to each other. The large solid state sensor assembly is preferably a solid state X-ray assembly and includes at least a first solid state sensor having an X-ray detector region and a blind non-detector border region, and a second solid state sensor having an X-ray detector region and a blind non-detector border region. The second sensor is positioned adjacent to the first sensor with respective non-detector regions being contiguous. A third solid state sensor having an X-ray detector region, is positioned to overlie the first and second solid state sensors so that the X-ray detector region of the third sensor overlies the blind non-detector regions of the first and second sensors. Thus, a large continuous X-ray detector region formed of said first, second, and third sensor detector regions is provided. The three sensors have a plurality of solid state detectors, with the detectors of the third sensor being smaller in size then the detectors of first and second sensors.

8 Claims, 3 Drawing Sheets

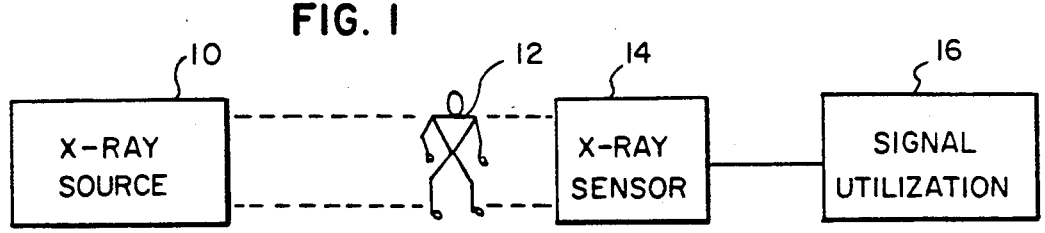
FIG. 1
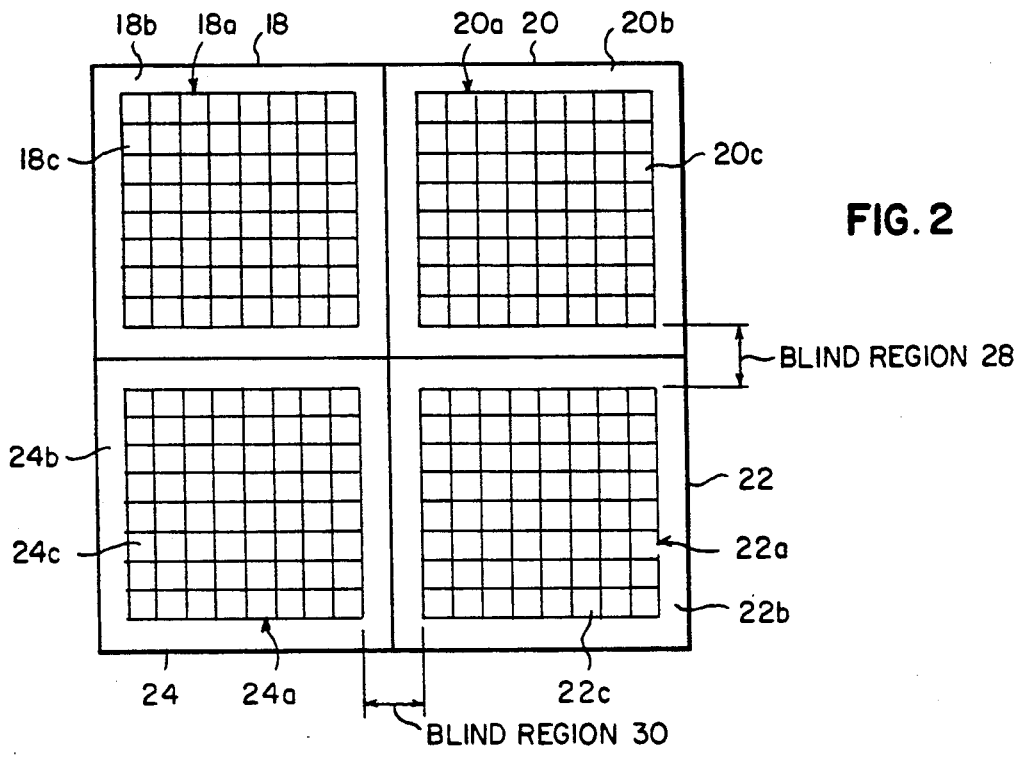
FIG. 2
FIG. 3

LARGE SOLID STATE SENSOR ASSEMBLY FORMED FROM SMALLER SENSORS

BACKGROUND OF THE INVENTION

This invention relates in general to apparatus for sensing radiation such as X-rays and, more particularly, relates to a large solid state X-ray sensor assembly formed of smaller solid state X-ray sensor assemblies in which blind non detector regions are eliminated.

X-ray detection systems are used widely in medical and industrial applications to image the interior of a structure in a non-invasive manner. Typically, an X-ray system includes a source of X-rays, which are directed to penetrate a region of interest of an object, and X-ray sensitive film which forms an image of the irradiated region of the object. The latent image in the film must be developed before it is available for examination and diagnosis. In order to simplify and speed up the X-ray examination system, various electronic detection systems have evolved. Older systems have utilized scintillators or other X-ray sensitive devices to convert an X-ray image into a visible image. The visible image is then detected by means of an array of Photomultiplier tubes or a cathode ray tube to convert the visible image into an electrical image representative of the X-ray image. The electrical image may then be processed electrically to enhance, display or store the image.

More recently, solid state semi conductor sensors have replaced photomultiplier tubes and cathode ray tubes as visible image detectors. The solid state sensors are combined with X-ray sensitive phosphors or X-ray sensitive image intensifier arrangements. However, the sequential conversion of an X-ray image into a visible image and then to an electrical image is disadvantageous because of reduced sensitivity and resolution as compared to a system which is capable of directly converting an X-ray image into a corresponding electrical image. Moreover, currently available solid state or cathode ray tube X-ray systems are not large enough to image the area of the largest X-ray film. Thus, the frequently used chest X-ray film has a 14×17 inch size whereas present day single crystal semi conductor solid state sensors are considerably smaller in size.

There is also a need for a simple, inexpensive and large solid state sensor assembly which senses other types of radiation (such as light) than X-rays.

SUMMARY OF THE INVENTION

In general, according to the present invention, there is provided a large solid state sensor assembly formed from a plurality of smaller solid state sensors. A large radiation sensitive region is effected by filling in blind, non sensor regions between contiguous sensor regions by means of smaller solid state radiation sensors.

According to a feature of the present invention, there is provided a solid state X-ray sensor assembly which directly converts an X-ray image into a corresponding electrical image. According to another feature of the present invention, a large solid state X-ray sensor assembly is formed from a Plurality of smaller solid state X-ray sensors. A large X-ray sensitive region is effected by filling in blind non sensor regions between contiguous X-ray sensor regions by means of small solid state X-ray sensors.

BRIEF DESCRIPTION OF THE DRAWINGS

On the detailed description of the accompanying drawings in which like elements are numbered with like numbers.

FIG. 1 is a partially diagrammatic, block diagram of an X-ray system including an embodiment of the present invention.

FIGS. 2 and 3 are diagrammatic views of solid state sensors which are useful in describing the present invention;

DESCRIPTION OF THE PREFERRED EMBODIMENT

Figure 4:
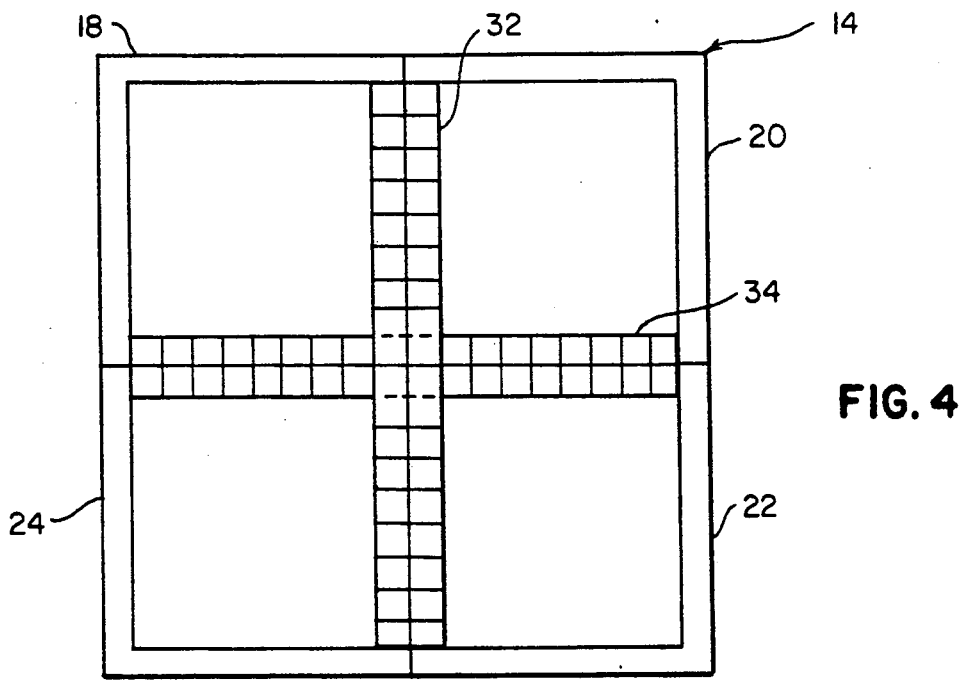
FIG. 4 is a diagrammatic view of one embodiment of the present invention.

Referring now to FIG. 1, there is shown a medical X-ray system incorporating an embodiment of the present invention. It will be understood that scientific applications. It will also be understood radiation other than X-rays may be sensed by the sensor assembly of the present invention. As shown, a source 10 of X-rays directs X-rays through the region of interest of the body of an individual 12. An X-ray image of the region is detected by X-ray sensor apparatus 14. Apparatus 14 directly detects the X-ray image and converts it into an electrical signal which is provided to signal utilization device 16. Device 16 may, for example, be a video monitor for displaying the X-ray image or a magnetic or optical storage device for storing the electrical image in digital form.

Since conventional X-ray film comes in a variety of sizes (the size for chest X-rays being one of the largest at 14 inches by 17 inches), X-ray sensor 14 is sized to detect the largest X-ray image. However, because present day solid state sensor technology is limited to sensor sizes smaller than 14–17 inches (except in very expensive custom built applications), in order to detect a large X-ray image using solid state sensors of commonly available sizes, according to the present invention, a number of sensors are grouped together to form a large sensor assembly. Typically, a solid state sensor has an active detector region including an array of solid state X-ray detectors and a blind non detector border region which accommodates input and output terminals and related circuitry. When a Plurality of smaller sensors are grouped together to form a larger sensor assembly, blind regions containing no radiation detectors result.

This is illustrated in FIG. 2, which shows solid state sensors 18, 20, 22, and 24 grouped together to form a larger sensor assembly. Each solid state sensor respectively includes a radiation detector region 18a, 20a, 22a, and 24a, and a blind non detector region. 18b, 20b, 22b, and 24b. Detector regions 18a, 20a, 22a, and 24a include two dimensional arrays of individual detectors 18c, 20c, 22c, and 24c, respectively. Solid state detectors may be of any semiconductor which is capable of directly detecting X-rays. Suitable semiconductors are germanium, cadmium sulfide/selenium, etc.

Blind non detector regions 28 and 30 are formed by segments of blind border regions 18b, 20b, 22b, and 24b. Thus, an X-ray image would be imperfectly detected by sensors 18, 20, 22, and 24 and would have non detected portions thereof missing in the electrical image produced by the sensors. Thus, because the region of greatest diagnostic interest in the X-ray image may be excluded, such a sensor assembly is impractical. According to the present invention, a large solid state X-ray sensor assembly includes a plurality of contiguous smaller solid state X-ray sensors having additional solid state X-ray sensors overlying the blind non detector regions 28 and 30. Thus, an entire large X-ray image is detected without missing image regions. As shown in FIG. 3, elongated sensors 32 and 34 have detector regions which are dimensioned to fill in blind regions 28 and 30. In FIG. 4, elongated solid state sensor 32 overlies the blind region 30 of the sensor assembly of FIG. 2 and elongated solid state sensor 34 overlies blind region 28 of the sensor assembly of FIG. 2.

Thus, in the embodiment shown in FIG. 4, a continuous X-ray detection region is formed from the composite detector regions of solid state sensors 18, 20, 22, and 24 and elongated sensors 32 and 34.

Figure 5:
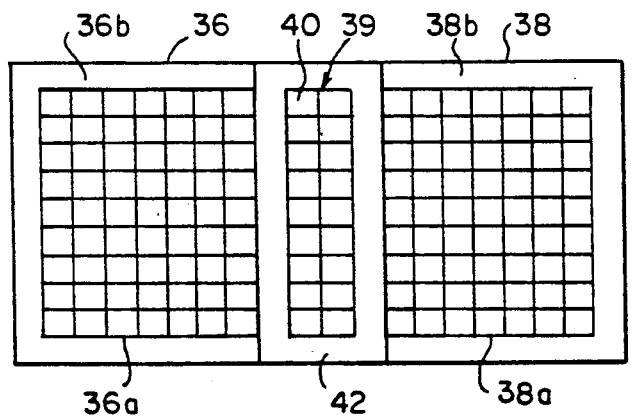
FIG. 5 is a diagrammatic view of another embodiment of the present invention.

Referring now to FIG. 5, there is shown another embodiment of the present invention. As shown, solid state sensors 36 and 38 include two-dimensional arrays of solid state X-ray detectors 36a and 38a. Sensor 39 having a one dimensional array of X-ray detectors 40 overlies the blind region 42 formed by blind non detector border regions 36b and 38b of detectors 36 and 38 respectively.

Figure 6:
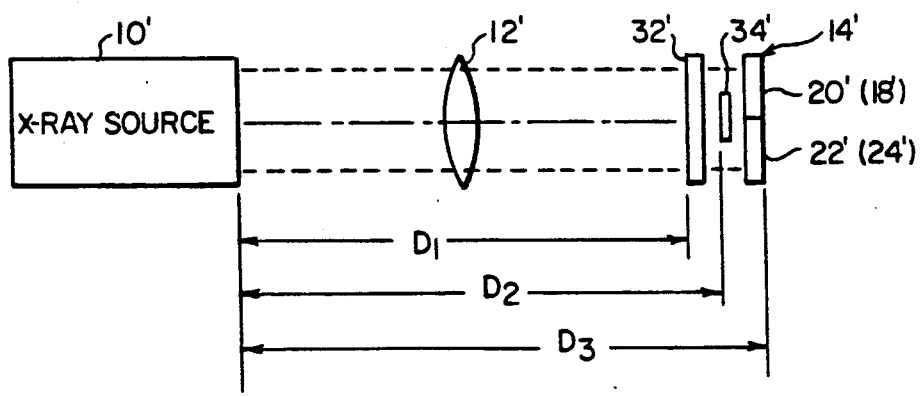
FIGS. 6 and 7 are respectively elevational and exploded views of another embodiment of the present invention.
Figure 7:
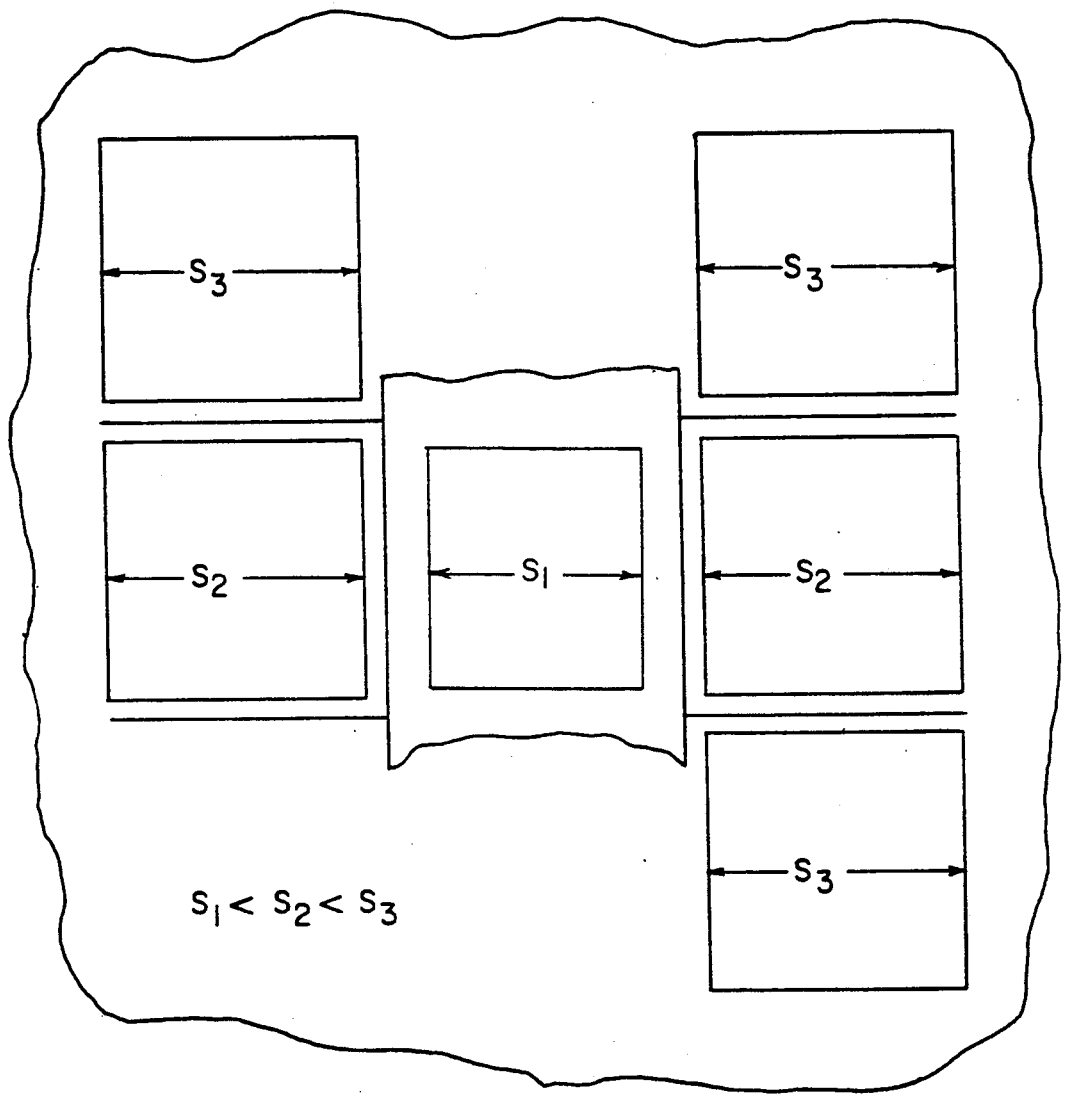

Referring now to FIGS. 6 and 7, there is shown another embodiment of the present invention. As shown in FIG. 6, X-ray source 10' directs X-rays through object 12' to form an X-ray image which is detected by solid state X-ray sensor assembly 14' of the type shown in FIG. 4. Assembly 14' includes solid state sensors 20', 18', 22', and 24' which are formed into a large solid state X-ray sensor assembly. Assembly 14' includes elongated sensors 32' and 34' which overlie the blind regions formed by the non detecting borders of sensors 18', 20', 22', and 24' (See FIG. 4). As depicted in FIG. 6, sensors 18', 20', 22', and 24' are coplanar and located at a distance $D_3$ from X-ray source 10'. sensor 34' is located at a distance $D_2$ from X-ray source 10', and sensor 32' is located at a distance $D_1$ from X-ray source 10'. In order to equalize the sensitivity of the X-ray detectors which are located at different distances from X-ray source 10', according to another embodiment of the present invention, the size of X-ray detectors increases as the distance of the detector from the X-ray source increases. Thus, as shown in FIG. 7, the size $S_1$ of a detector of sensor 32' is less than the size $S_2$ of an X-ray detector of sensor 34' which is less than the size $S_3$ of an X-ray detector of sensors 18', 20', 22', and 24'.

Although specific embodiments of the present invention have been described and shown herein, it will be understood that variations and modifications of thereof are within the knowledge of one skilled in the art. Thus, a large solid state X-ray sensor assembly may include any number of number of corresponding overlying sensor arrays to effect a continuous X-ray detector array. Moreover, the embodiments of the invention described above may be configured to sense radiation images other than X-ray images. Thus, sensor assemblies according to the invention may sense radiation images in the ultraviolet, visible and infrared regions, in the alpha, beta and gamma regions etc.

The invention has been described in detail with particular reference to a preferred embodiments thereof. But it will be understood that variations and modifications can be effected within the scope and spirit of the invention.

What is claimed is:

1. For use with a radiation source, a solid state radiation sensor assembly comprising:
    a first solid state sensor having a radiation detector region and a blind non-detector border region;
    a second solid state sensor having a radiation detector region and a blind non-detector border region; said second sensor being positioned adjacent to said first sensor such that said non-detector regions of said first and second sensors are contiguous;
    a third solid state sensor having a radiation detector regions, said third sensor overlying said first and second sensors so that said radiation detector region of said third sensor is positioned over said blind nondetector regions of said first and second sensors and forms a continuous radiation detection region with the radiation detector regions of said first and second radiation sensors; and
    wherein said first, second and third sensors respectively have a plurality of solid state radiation detectors such that said detectors of said third sensor are smaller in size than said detectors of said first and second sensors.

2. The assembly of claim 1 wherein said first and second sensors have respective two dimensional arrays of solid state radiation detectors and wherein said third sensor has an array of radiation detectors which are aligned with the detectors of said first and second sensors.

3. The assembly of claim 1 wherein said first, second, and third solid state sensors are made of germanium semiconductor.

4. The assembly of claim 1 wherein said first, second, and third solid state sensors are made of cadmium sulfide/selenium semiconductor.

5. For use with an X-ray source, a solid state X-ray sensor assembly comprising:
    a first solid state sensor having an X-ray detector region and a blind non-detector border region;
    a second solid state sensor having an X-ray detector region and a blind non-detector border region; said second sensor being positioned adjacent to said first sensor such that said non-detector regions of said first and second sensors are contiguous; and
    a third solid state sensor having an X-ray detector region, said third sensor overlying said first and second sensors so that said X-ray detector region of said third sensor is positioned over said blind non-detector regions of said first and second sensor and forms a continuous X-ray detection region with the X-ray detector regions of said first and second X-ray sensors; and
    wherein said first, second and third sensors respectively have a plurality of solid state X-ray detectors such that said detectors of said third sensor are smaller in size than said detectors of said first and second sensors.

6. The assembly of claim 5 wherein said first and second sensors have respective two dimensional arrays of solid state X-ray detectors and wherein said third sensor has an array of X-ray detectors which are aligned with the detectors of said first and second sensors.

7. The assembly of claim 5 wherein said first, second, and third solid state sensors are made of germanium semiconductor.

8. The assembly of claim 5 wherein said first, second, and third solid state sensors are made of cadmium sulfide/selenium semiconductor.

* * * * *